United States Patent
Bader

(10) Patent No.: US 7,910,547 B2
(45) Date of Patent: Mar. 22, 2011

(54) TISSUE REGENERATION METHOD

(75) Inventor: Augustinus Bader, Parthenstein OT Klinga (DE)

(73) Assignee: Augustinus Bader, Parthenstein OT Klinga (DE)

( * ) Notice: Subject to any disclaimer, the term of this patent is extended or adjusted under 35 U.S.C. 154(b) by 225 days.

(21) Appl. No.: 10/583,879

(22) PCT Filed: Dec. 30, 2004

(86) PCT No.: PCT/EP2004/014839
§ 371 (c)(1),
(2), (4) Date: Apr. 9, 2007

(87) PCT Pub. No.: WO2005/063965
PCT Pub. Date: Jul. 14, 2005

(65) Prior Publication Data
US 2008/0031850 A1    Feb. 7, 2008

(30) Foreign Application Priority Data
Dec. 30, 2003 (DE) ................................ 103 61 813
Dec. 30, 2003 (EP) ................................. 03029961

(51) Int. Cl.
*A61K 38/18* (2006.01)
*C07K 14/505* (2006.01)
(52) U.S. Cl. ........................................ 514/7.7; 530/397
(58) Field of Classification Search ........................ None
See application file for complete search history.

(56) References Cited

U.S. PATENT DOCUMENTS

| | | | |
|---|---|---|---|
| 6,479,064 B1 | 11/2002 | Atala et al. | |
| 2002/0187936 A1 | 12/2002 | Costa et al. | |
| 2003/0096407 A1 | 5/2003 | Atala et al. | |
| 2003/0104988 A1 * | 6/2003 | Brines et al. | 514/8 |
| 2004/0136952 A1 * | 7/2004 | Bhaskaran et al. | 424/85.1 |
| 2006/0035374 A1 | 2/2006 | Bader | |

FOREIGN PATENT DOCUMENTS

| | | |
|---|---|---|
| EP | 1077254 A2 | 2/2001 |
| WO | WO 99/21966 | 3/1999 |
| WO | WO 99/21966 * | 5/1999 |
| WO | WO 01/13936 | 3/2001 |
| WO | WO 04/001023 | 12/2003 |

OTHER PUBLICATIONS

Maggi et al. The efficacy of 5% sulfamylon solution for the treatment of contaminated explanted human meshed skin grafts. Burns vol. 25:237-241 (1999).*
Buemi et al. Recombinant human erythropoietin influences revascularization and healing in a rat model of random ischaemic flaps. Acta Derm Venereol. 82:411-417 (2002).*
Dunn, J. M. Local wound care in the diabetic. Abstract; Clinics in podiatric medicine and surgery, vol. 4/No. 2, pp. 413-418, (Apr. 1987).*
Kim et al. Experience with patients with burns who refuse blood transfusion for religious reason. Journal of Burn Care & Rehabilitation. vol. 14(5):541-3 (Sep.-Oct. 1993).*
Fedorov et al. "Functional and Morphological Changes and Liver Regeneration After Liver Resection," *PubMed*: 8246391 (1993) (abstract).
Michalopoulus et al., "Liver Regeneration," *Science* 276:60-66 (1997).

* cited by examiner

*Primary Examiner* — Marianne P Allen
*Assistant Examiner* — Regina M DeBerry
(74) *Attorney, Agent, or Firm* — Clark & Elbing LLP

(57) ABSTRACT

The invention relates to the use of haematopoietic growth factors, in particular erythropoietin (EPO) and thrombopoietin (TPO), or derivatives, analogues or parts thereof, for promoting structural tissue regeneration.

3 Claims, No Drawings

TISSUE REGENERATION METHOD

CROSS REFERENCE TO RELATED APPLICATIONS

This application is the U.S. National Stage of International Application No. PCT/EP2004/014839, filed Dec. 30, 2004, which claims benefit of German patent application no. 10361813.9, filed Dec. 30, 2003 and European patent application no. 03029961.4, filed Dec. 30, 2003, hereby incorporated by reference.

The present invention relates to a method for the induction of structural growth of tissue, in particular in liver regeneration, and claims the priorities of German Patent Application 103 61 813.9-41 and European Patent Application 03 029 961.4, the contents of which are incorporated herein by way of reference.

In ontogenesis, growth factors are expressed which are able to trigger basic structural and, with respect to the cell count, numerical processes for the synthesis of a tissue. In the growing organism and adult organism, the ability to synthesise or—in the case of tissue damage—to regenerate structurally and functionally intact tissue is, however, substantially lost. It is assumed that the reduced expression of growth factors, which in turn control the expression of proteins necessary for tissue synthesis, is responsible for this reduction in regenerative ability.

However, it is known of at least some organs that, even in the adult organism, they retain an ability for self-regeneration which can be induced by injury processes. Thus, for example, the regenerative capacity of the liver has already been known since antiquity. Virtually all other organs cannot of their own accord correspondingly bridge structural defects in order to restore the original tissue.

The liver in the adult organism is generally in the resting, i.e. non-proliferating state, in which the organ has to fulfil a complex variety of different metabolic functions. In vivo, however, the liver is re-stimulated to growth by the loss of cell mass—for example due to liver cell damage or due to a surgical intervention.

However, proliferating liver tissue usually does not replace the functional and anatomical structures of the organ in the desired manner, but instead generally results in enlargement and hypertrophy of the remaining liver tissue until the original liver cell mass has been replaced. The intensity of the growth response is dependent on the extent of the tissue loss. The course of liver regeneration over time has an inversely proportional correlation here, i.e. small liver cell losses are replaced slowly, large liver cell losses significantly more quickly.

The replacement of the organ mass by cell proliferation alone therefore does not represent an adequate basis for therapy of a patient with considerable organ damage. Various approaches for the induction of structural growth—i.e. for shape-creating growth—of tissues are therefore known, but none has yet resulted in satisfactory success. However, such structural growth of cells would be of considerable importance, especially for therapeutic or biotechnological methods.

In the past, it has been attempted to induce growth of cells by the administration of growth factors, such as, for example, "epidermal growth factor" (EGF), "vascular endothelial growth factor" (VEGF) or "hepatocyte growth factor" (HGF). However, the effect of these factors on the reproduction of primary cells in vitro is limited. By contrast, their use in vivo is not unproblematic owing to their possible side effects—for example activation of oncogenes.

Another approach is based on the use of complex heterologous tissue extracts, for example from the pituitary gland or the hypothalamus, for the induction of cell reproduction, for example of cultivated hepatocytes (see, for example, U.S. Pat. No. 6,008,047). However, the use of animal or human tissue extracts is problematic against the background of transmissible viral diseases, such as, for example, BSE, pig or sheep viruses, in laboratory operations or in clinical use and tends to document the lack of knowledge about the processes involved in the synthesis of complex organ structures and about the factors that are actually relevant and their use and action potentials. In addition, the extracts are difficult to define in their quality, since this is dependent, inter alia, on the source and the cultivation conditions thereof.

Even the little knowledge from the classical applications of primary tissue cultures cannot, however, be applied directly to the questions of tissue engineering. Thus, tissue engineering generally ideally starts from patient-specific, adult cell systems which have already differentiated further than foetal or embryonic cells. In addition, tissue engineering both in situ and in vitro relates to co-culture situations, which are not taken into account in the classical application. Indeed, it is on the contrary much rather attempted to avoid co-cultures of endothelial cells, macrophages and fibroblasts, as occur in the liver, in the expansion of parenchymal liver cells as they are undesired.

It is known from WO 02/092013 A2 to administer a therapeutically effective amount of growth hormone (GH) to a patient for the treatment of liver damage in order thus to promote the natural regeneration capacity of the liver. According to this specification, GH has the effect of accelerating expression of the growth factor Fox M1B in hepatocytes and thus re-initiating liver growth.

However, growth hormone has a very broad and therefore non-specific action on the growth of tissues. GH administration therefore also produces undesired side effects or overreactions, for example in the form of so-called acromegaly, i.e. excessive ossification with pathological bone states. Furthermore, it has in the meantime been disclosed that Fox1M is up-regulated in basal cell carcinomas. The Fox proteins play an important role in the regulation of growth genes in reproduction, differentiation and transformation, including in the activation of so-called SONIC HEDGEHOG (Shh) signalling pathways. These in turn are involved in the activation of basal cell carcinomas in human skin. Thus, Teh et al. (Cancer Research 2002, Aug. 15; 62 (16): 4773-80) have been able to show that the upregulation of FoxM1 in basal cell carcinomas is one of the main initiation mechanisms by means of which the SONIC HEDGEHOG signalling pathways exert mitogenic effects in the basal keratinocytes, resulting in the development of the widespread human cancerous ulcer. This tumourigenic potential of Fox1M agonists and the low specificity and ubiquitous presence in all tissues therefore stands in the way of administration of GH for promoting liver regeneration.

The object of the present invention is therefore to provide a method which induces the induction of essentially structural growth of a tissue. This growth should preferably result in an essentially functional and structural functioning of the tissue in question.

This object is achieved in accordance with the invention by the use of haematopoietic cytokines, derivatives or analogues or parts thereof, for structural and functional liver regeneration. In a particularly preferred embodiment, erythropoietin (EPO) or a derivative, parts or analogue thereof is administered. However, the effect according to the invention on the tissue in question can also be achieved by the administration of thrombopoietin or parts thereof.

Surprisingly, it has been found that the administration of haematopoietic growth factors, such as EPO and TPO, not only initiates reproduction of the cells, but also structural growth. This growth commences, in particular, in previously traumatized tissues. The growth thereby induced results in vivo in tissue regeneration in the true sense, i.e. not only proliferative growth, but also directed, differentiated growth for the synthesis of complex structures occurs.

At its core, the use according to the invention of haematopoietic factors for tissue regeneration is essentially based on two previously unknown actions of EPO, namely firstly on stimulation of structural growth in synchronous and coordinated form of various cell types amongst one another and with one another (such as, for example, fibroblasts, smooth muscle cells with endothelial cells in the vascular area in combination with regeneration of the architecture of a complete vessel taking into account the extracellular matrix (collagen, elastin, fibronectin, entactin)) and completion of the actual parenchymal tissue association. This includes, for example, the formation of hepatocytes with the associated Kupffer cells, Pit Ito and endothelial cells (so-called non-parenchymal cells of the liver). Besides the formation of an actual vascular tree and the interconnection thereof, tissue regeneration in the sense of restitutio ad integrum is thus induced in accordance with the invention.

In the liver, this results in a mixture of sinusoidal capillaries in the terminal flow region and vascular feed and discharge vessels alongside the actual parenchymal association of the hepatocytes in an ordered 3D structure.

As already stated, the action according to the invention of the haematopoietic growth factors commences, in particular, in traumatized tissues and cells. The term trauma here is defined as contrast to the process of histogenesis (tissue formation). Accordingly, a trauma is a process which counters histogenesis as tissue formation process in the individual organism at the locations in question or negates the result of histogenesis. Trauma as tissue damage can be initiated by a multiplicity of events, for example by injuries, inflammation or by autoimmune diseases with self-damage). This tissue damage or destruction in turn initiates a multiplicity of reactions, for example the activation of macrophages, mast cells and immunocompetent cells, which secrete chemotactic, vasoactive and wound healing-promoting factors and thereby regulate systemic and regioselective mechanisms.

The advantages of the use according to the invention of haematopoietic growth factors, in particular EPO, extend to the regeneration of tissues of all four basic tissue types, namely connective tissue, muscle tissue, epithelial tissue and nerve tissue. This tissue is derived ontogenetically either from the mesoderm (connective tissue, muscle, endothelium (as particular form of the epithelium)), the endoderm (the epithelium lining the gastrointestinal tract) or the ectoderm (nerve tissue). It has been shown in the past that the EPO receptor is expressed both on cells of meso- and endo-dermal origin and on neuronal cells.

In these tissues, the use according to the invention of EPO or TPO results in local recruitment of the tissue-specific progenito population (stem cells), migration of the cells and differentiation or transdifferentiation of the cells in parenchymal and structural cells. During and before this tissue formation, the cells multiply due to the administration of EPO.

On use of the method according to the invention, for example, for liver regeneration, re-completion of the previously damaged organ can be achieved to give a complete parenchymal tissue association, including the formation of hepatocytes with Kupffer cells, Pit, Ito and endothelial cells. With the continued formation of a vascular tree, tissue regeneration is thus possible in accordance with the invention as restitutio ad integrum.

It is thus a particular advantage of the method according to the invention that not only is microcapillarization of the regenerating tissue stimulated via endothelial sprouting, but also parenchymal regeneration and the formation of wall structures are promoted. Only this results in the desired result of coordinated three-dimensional growth for the synthesis of a functioning organ.

The use according to the invention is thus based on an EPO action which goes well beyond the EPO action known to date as angiogenetic factor on endothelial cell reproduction (Journal of Nephrology 2002 15, 97 to 103). Since microvascular structures, such as capillaries and sinusoids, merely consist of endothelial cell lining and do not have their own wall structure, however, it has hitherto only been possible, on the basis of the angiogenetic action of EPO, to speculate on whether EPO could also have a certain importance in revascularization and wound healing (Journal of Nephrology 2002 15, 97 to 103). However, these speculations have hitherto not been substantiated.

It is therefore all the more significant here that evidence of the action of EPO on the synchronized and coordinated growth of the vessels themselves, i.e. including the formation of the wall structures and parenchymal regeneration, has been provided for the first time.

A further advantage of the method according to the invention consists in that the structural growth does not necessarily require a prespecified organic or inorganic three-dimensional structure as starting point, but instead creates an organ (part-) structure de novo. The administration of haematopoietic growth factors can thus induce significantly accelerated self-regeneration of damaged tissue, which is of great importance in the clinical-therapeutic application of the invention.

In a particularly advantageous embodiment of the invention, the haematopoietic growth factors are employed to induce regeneration of a tissue which has traumatically damaged regions. In these tissue sections, not only can closure of the wound be stimulated by the formation of a granulation tissue with commencing angiogenesis, but also the re-formation of the tissue-specific three-dimensional structure from extracellular matrix, for example from collagen, elastin, fibronectin or entactin.

In accordance with the invention, haematopoietic growth factors are employed. These are, in particular, thrombopoietin, erythropoietin and growth hormone (GH) and functionally and structurally homologous analogues, derivatives and/or parts thereof. In particular, however, EPO or TPO or parts, derivatives or analogues thereof are employed. Mimetic peptides thereof (see below) are also suitable. The haematopoietic growth factors furthermore include G-CSF and GM-CSF.

The haematopoietic growth factors are left-handed quadruple-helix bundle proteins with an up-up-down-down orientation with two overlapping loops which connect the first two and the last two helix structures to one another (Livnah O. et al., Science 1999, 283 (5404): 987-90 and Ultsch M. H. et al, Blood 1995, 86 (2): 540-7. The respective RBD domains (receptor-binding domains) have pronounced homology with EPO. Thrombopoietin, erythropoietin and growth hormone bind to the MPL receptor complex. In the publication by Youssoufianh et al. in Blood 1993, 819 2223 to 36, Structure function and activation of the Erythropoietin receptor), a productive dimerization is described. Erythropoietin and thrombopoietin, mimetic peptides (EMP and DMP) and furthermore non-peptidic small molecules are likewise functional, although on a lower molar basis (publications: Wrighton N C et al. Small peptides as mimetics of the protein hormone erythropoietin Science 1996, 273 (5274) 458-64 and Cwirla S E et al. Peptide agonist of the thrombopoietin receptor as potent as the natural cytokine, Science 1997, 27653191696-9 and Qureshi S. A. et al. Mimicry of Erythropoietin by non peptide molecules, Proceedings National Academy of Sciences PNAS USA 1999, (9621): 12156-61). The binding of EMP 1 to the receptor takes place at binding sites which are homologous with the hot spots of growth hormone receptor compounds. The structural sequences of thrombopoietin are described in detail in EP 1 201 246 A2. The structural sequences of erythropoietin are described in detail in European Patent Application EP 84 308 654.7.

A particularly advantageous embodiment of the invention makes use of EPO which stimulates in vivo the formation of erythrocytes and cell division and differentiation of erythrocyte precursor cells. EPO can either be isolated from urine or prepared by recombinant methods. The preparation of a recombinant human EPO is the subject-matter of WO 86/03520. Furthermore, EPO is the subject-matter of EP 0 148 605, EP 0 205 564, EP 0 209 539, EP 0 267 678 or EP 0 411 678.

However, it is also possible to employ derivatives of native or recombinant EPO. Thus, for example, an EPO derivative is known (EP 0 640 619 B1) which has additional glycosylation sites and thus a higher carbohydrate content with 22 sialic acid residues. The advantage of this modification consists in that the half-value period of EPO in the plasma increases with an increased content of sisalic acid, since only a non-sialated EPO is able to bind to the liver galactose receptor involved in EPO degradation. Although this EPO derivative—known under the abbreviation NESP (novel erythropoiesis stimulating protein or darbepoetin)—has an amino acid sequence which is modified in five positions compared with recombinant EPO, it essentially corresponds in its action on the stimulation of erythrocyte formation to native or recombinant EPO (Fisher, J. W.: Erythropoietin: Physiology and Pharmacology Update. Erythropoietin 2003, 1-14). EP 0 640 619 B1 is incorporated herein by way of reference in its full scope with respect to the structure and preparation of NESP.

NESP can advantageously also be chemically conjugated with polyethylene glycol (PEG) for further extension of the in vivo half-value period without a change in the biological activity being associated therewith. An NESP modified in this way is known from WO 01/76640, which is incorporated herein by way of reference in its full scope with respect to the structure and preparation of this EPO derivative.

WO 02/49673 A2 and WO 01/02017 A2 likewise disclose pegylated derivatives of EPO which, besides the extended plasma half-value period, also exhibit higher clinical efficacy. To this end, for example, 1 to 6 additional glycosylation sites are introduced into the EPO amino acid sequence by targeted mutagenesis. This derivative can likewise be employed in accordance with the invention.

Besides EPO and EPO derivatives having a corresponding biological function, other haematopoietic growth factors, such as, for example, TPO or parts thereof, can also be employed in accordance with the invention.

TPO (also known as c-Mpl ligand, mpl ligand, megapoietin or megakaryocyte growth and development factor) is a haematopoietic growth factor having a complex biological action, which regulates, inter alia, the development and proliferation of megakaryocytes and thrombocytes. Mature TPO consists of a sequence of 332 amino acids, where the N-terminal region (RBD domain) having 154 amino acids has considerable sequence and structural homology with EPO (20% identity and a further 25% similarity). In particular, TPO forms two highly preserved cysteine bridges, which are also found in homologous positions in EPO.

It has been shown in the past that the N-terminal region of TPO is responsible for the binding to the cytokine receptor and the signal cascade induced thereby via the JAK/STAT pathway (Geddis A. E., Linden H. M., Kaushansky K: Thrombopoietin: a pan-haematopoietic cytokine. Cytokine & Growth Factor Reviews 13 (2002) 61-73). In accordance with the invention, it is therefore again only possible to use part of the TPO, in particular the N-terminal fragment.

The preparation and characterization of TPO and variants thereof are described, for example, in EP 1 201 246, WO95/21919, WO95/21920 and WO95/26746. These are incorporated herein in their full scope by way of reference for disclosure purposes. The action of TPO on foetal hepatocytes is known from investigations by E. Schmelzer (E. Schmelzer: Optimierung der Kultur und Charakterisierung primärer embryonaler Hepatozyten der Ratte [Optimization of the Culturing and Characterization of Primary Embryonic Rat Hepatocytes]; Dissertation Göttingen 2002).

Suitable variants of TPO are, for example, the TPO derivatives described in WO95/21919 or the allelic variants or species homologues described in WO95/21920 or the pegylated TPO described in WO95/26746 and EP 1 201 246, without being restricted thereto. For the purposes of the present invention, pegylated TPO is taken to mean TPO derivatives which are bound to an organic polymer, such as, for example, polyethylene glycol, polypropylene glycol or polyoxyalkylene. Further variants of TPO are also taken to mean derivatives of TPO which have a sequence identity of less than 100% and nevertheless have the activity of TPO, as preferably described in EP 1 201 246. TPO derivatives usually have a sequence identity of at least 70%, preferably at least 75%, in particular at least 80% and especially at least 85% compared with human TPO, including fragments thereof having TPO activity. A particularly preferred TPO activity for the purposes of the present invention is the acceleration of proliferation, differentiation and/or maturing of megakaryocytes or megakaryocyte precursors in platelet-producing forms of these cells by TPO or variants thereof.

In accordance with the invention, EPO and TPO can be employed both in their human and non-human form. Thus, for example, human TPO have a homology of greater than 70% with pig or mouse TPO.

In an alternative embodiment of the invention, it is possible to administer to the patient not the haematopoietic growth factors themselves, but instead factors which induce the expression of the growth factors in the traumatized tissues.

Thus, it is described, for example, by Naughton B A et al (Age-related variations in hepatic regeneration and erythropoietin production in the rat, Am J Anat. 1977 July;149(3): 431-8) that erythropoietin is principally formed in the liver and spleen during neonatal phases and that, in the case of nephrectomy, the phenomenon of hepatic EPO formation can increase again after a hepatectomy. This ability decreases with age. It was then later recognized (Hepatic regeneration and erythropoietin production in the rat. Naughton B A, Kaplan S M, Roy M, Burdowski A J, Gordon A S, Piliero S J. Science, 1977 Apr. 15;196(4287):301-2) that a regenerating liver produces erythropoietin as a response to hypoxia. It has been found that the EPO production is dependent on the liver regeneration stage, with the highest EPO concentrations being found in the phase of strongest liver growth.

Dornfest et al. described in 1981 (Recovery of an erythropoietin inducing factor from the regenerating rat liver. Dornfest B S, Naughton B A, Kolks G A, Liu P, Piliero S J, Gordon A S. Ann Clin Lab Sci. 1981 January-February;11(1):37-46) that the liver is the principal source of the formation of an EPO-inducing factor. In the case of nephrectomy, the formation of the factor in the liver increased. The EPO action according to the invention can thus also be achieved indirectly by the administration of a factor which induces the expression of EPO.

Endogenous EPO expression can likewise be achieved, for example, by the stimulation of EPO secretion by the medium- or long-term administration of growth hormone (GH) (Sohmiya, M., Y. Kato. Effect of long-term administration of recombinant human growth hormone (rhGH) on the plasma erythropoietin (EPO) and haemoglobin levels in anaemic patients with adult GH deficiency. Clinical Endocrinology (2001) 55, 749-754).

The individual concentrations of the growth factors in solution can be about 1 to about 100 ng/ml, preferably about 10 to about 50 ng/ml, in particular about 10 to about 20 ng/ml. In the case of local coatings (topical administration), however, the concentrations of the growth factors may also be a multiple thereof.

The haematopoietic growth factors can advantageously also be employed for the cultivation of tissue cultures in vitro. To this end, the cells are cultivated in apparatuses and by methods which are particularly suitable for the tissue, for example on a mesh having an intersecting net structure having a size of 500 m in order always to allow new daughter aggregates of hepatocytes to form. In particular in vitro, combinations of EPO with GH are advantageous.

In particular, it is possible to employ non-contact, automatically or manually controlled pump systems which consist, for example, of piston pumps or produce directed streams produced magnetically or by compressed-air compression of hoses. In the presence of endothelial cells, the shear stress in a perfused bioreactor can result in spontaneous confluence of the endothelial cells on the surfaces of the aggregates, which may be advantageous for further use.

Suitable for the encapsulation are suitable materials known to the person skilled in the art into which, for example, structured shapes or chambers are integrated, facilitating an in situ growth structure or enlargement. Alternatively, the capsules can be omitted and endothelialization and thus optimum haemocompatibility are achieved, for example, in the presence of endothelial cells.

The EPO or TPO administration according to the invention results either alone or, in the case of relatively large structural defects, also in combination with scaffold materials in biological tissue replacement. These support materials may have been pre-colonized in vitro or extracorporeally, be biologically modellable (biodegradable) and in the ideal case are micro- and macrostructurally and biochemically as similar as possible to the structure to be replaced. The biochemical proximity or identity includes a reconstruction of the in vivo composition by collagens and matrix proteins (elastin, fibronectin and all matrix components of the body in tissue-specific shaping, as known).

Stem cells can be obtained from the various source present in the patient's body: bone marrow, peripheral blood, fatty tissue, the tissue itself, umbilical cord blood or tissue. Allogeneic stem cells can be obtained correspondingly, but are afflicted with immunological disadvantages. Embryonic cells can be used, but are afflicted with the corresponding disadvantages.

In a particularly preferred embodiment, the structured growth process of the cultivated cells can be induced by a matrix coated with the growth factors according to the invention. To this end, the matrix can be treated sequentially with one or more of the said growth factors.

In the case of a biological matrix, the latter is usually an implant (stent, patch or catheter), a graft (for example skin graft), a support material for the growth of cells, for example a so-called slow-release material (for example a hydrogel based on fibrin and/or polymers, such as, for example, polylactide or polyhydroxyalkanoate, and/or alginates), a bone replacement material (for example tricalcium phosphate), an allogeneic, autologous or xenogeneic acellularized or non-acellularized tissue (for example heart valve, venous valve, arterial valve, skin, vessel, aorta, tendon, cornea, cartilage, bone, trachea, nerve, meniscus, diskus intervertebralis, ureters, urethra or bladder (see, for example, EP 0 989 867 or EP 1 172 120)), or a matrix (for example a laminin, collagen IV and/or matrigel matrix) or preferably a feeder layer, such as, for example, collagen I, 3T3 and/or MRC-5 feeder layer, or a collagen fleece.

The biological matrix is advantageously pre-colonized with tissue-specific cells, precursor cells, bone marrow cells, peripheral blood, fatty tissue and/or fibrous tissue, for example with adult precursor cells from the bone marrow. The pre-colonization results in the regeneration process already commencing in vitro, in order that the regeneration time in vivo after implantation of the matrix into the body is shortened.

The matrices used may also be activated in advance. The activation of the biological matrix or support structure can be carried out, for example, by means of plasma ionization, for example using hydrogen peroxide, or by means of laser activation.

Alternatively, coating with a biodegradable (bio)polymer layer which comprises the said growth factor(s) can be carried out. Suitable for this purpose are, for example, fibrin, plasma, blood, collagen and/or polylactides.

The method according to the invention is particularly suitable for adult cells, i.e. primarily differentiated cells, which no longer have an embryonic or foetal phenotype. It is particularly suitable for human adult cells, for example for adult progenitor cells, tissue-specific cells, preferably osteoblasts, fibroblasts, hepatocytes and/or smooth muscle cells.

Besides a termination or reduction in the supply of the growth factors described to the culture, somatostatin and/or TGF beta and/or prostaglandins are also suitable for termination of the growth process according to the invention.

It is particularly advantageous to employ methods according to the invention locally in vivo. To this end, the growth factors can be applied, for example, to the resection surface of an organ (for example a liver). They can be administered topically, or also locally or systemically with the aid of a catheter. In the case of a liver resection, they can alternatively or additionally be administered before, during or after the intervention. It is likewise possible to inject the growth factors (for example in order to promote cartilage regeneration) directly into the tissue or joint in question. The growth factors are thus able to act directly on the formation of a new cartilage structure via the synovial fluid.

In a particular embodiment, one or more of the following growth factors can be administered in addition to the haematopoietic growth factors: "transforming growth factor beta" (TGF beta), prostaglandins, granulocyte(macrophage)-stimulating factor (G(M)-CSF), "growth hormone releasing hormone" (GHRH), "thyrotropin-releasing hormone" (TRH), "gonadotropin-releasing hormone" (GnRH), "corticotropin-releasing hormone" (CRH), dopamine, "antidiuretic hormone" (ADH), oxytocin, prolactin, adrenocorticotropin, beta-celltropin, lutrotropin and/or vasopressin or additionally one or more nerve regeneration factors, preferably "nerve growth factor" (NGF) and/or one or more vascular regeneration factors, preferably "vascular endothelial growth factor" (VEGF) and/or "plateled derived growth factor" (PDGF).

The haematopoietic growth factors are administered parenterally as injectable microspheres, erodable particles, polymer compounds (with polypeptide, polyglycolic acid), liposomes and small particles. Injectable or implantable drug delivery devices are likewise possible. The substances may also be inhaled, injected subcutaneously, intramuscularly or—for topical application—administered as a cutaneous plaster.

In addition, substances which achieve local hyperaemia and thereby increase the skin permeability (for example bee venom) can be mixed with the plasters. Hyperionic structures with and without direct EPO coupling or coating of the salts can be transported better through the skin barriers and can be bound to preferably positively ionizing structures. Negative ionization is also possible. The factors can be used with almond oil or jojoba oil for improving transport through mucous membranes in the intestinal region or the skin.

Bonding to polyethylene glycol (PEG) is possible in order to overcome transport barriers (mucosa in the mouth, stomach, intestine; mucous membranes, cornea).

It is known that mixed preparations can be prepared from proteins. Suspensions, gel emulsions, solid compounds, dehydrated or lyophilized powders are possible. The growth factors can be absorbed onto particles or encapsulated.

It may be particularly advantageous to employ stem cells (progenitors in the true sense) together with EPO/TPO for tissue regeneration in order thus significantly to accelerate the recruitment of the tissue cells from the 4 basic tissue types for the regeneration process. EPO/TPO and the other factors mentioned can be administered as a mixture with stem cells and, for example, fibrin adhesive as support matrix. If necessary, the support matrix can be omitted or replaced by a more strongly pre-structured and shaped support matrix. The factors can also be administered systemically or topically without any biological support matrix, for example only in aqueous suspension.

The EPO administration according to the invention improves this tissue regeneration by tissue-specific shaping of the stem cells and differentiation subsequent to reproduction and integration and coordinates the growth in relation to the basic tissue types.

I. Areas of Application

1. Squamous Epithelia

EPO is employed in accordance with the invention to promote the formation of basal membranes (extracellular supporting layer under the epithelium). EPO supports the formation of the marginal region of the papillae.

EPO is employed in accordance with the invention to support the formation of glandular epithelium. EPO results in regeneration of plate-shaped cuboidal and columnar epithelia (squamous epithelium of the oesophagus, columnar epithelium in the seminal duct, transitional epithelium of the bladder).

EPO causes re-formation of the desmosomes, i.e. the connectors between the cells and their attachment structures, in the structural growth process. The formation of so-called microvilli on the epithelia, for example of the small intestine (epididymis, trachea).

EPO has a direct effect on the regeneration of the single-layered squamous epithelium, the endothelial lining of heart, blood and lymphatic vessels and the columnar epithelium (stomach, small and large intestine, gall bladder, fallopian tube, uterus). EPO is employed in accordance with the invention to form the double-layered epithelium (salivary glands of the oral cavity, nasolachrymal duct, duct of epididymis, seminal duct). EPO is also employed in accordance with the invention for the columnar epithelium (nasal cavity, epipharynx, larynx, tracheobronchial tree, urethra, eustachian tube), furthermore for the formation of uncornified and cornified squamous epithelium. The structure-promoting aspect on the parenchymal regeneration of EPO supports the formation of exocrine glands. These include, inter alia, the pancreas, glands in the epithelium of the small intestine (beaker cells, submandibular salivary gland, islet cells for insulin production). EPO supports the regeneration of the endocrine glands.

2. Connective Tissue

EPO is able to restore the basic constituents of the connective tissue in coordination with the surrounding parenchymal gland structures. The basic constituents which are affected thereby are the basic substance (glucosaminoglycans), the coordination with so-called plasma cells, fatty cells, blood vessels and surrounding smooth muscle cells, in addition the connective tissue cells, fibroblasts, mast cells and collagen fibres as well as the elastin fibres and inserted macrophage (likewise Kupffer, Pit, Ito cells in the liver) and capillary endothelial cells. Capillaries have only an endothelial cell lining.

However, EPO has a broader coordinative aspect on the outlined micro-environment here. This is put into an initiator state by traumatic injuries. EPO can be administered therapeutically in accordance with the invention if these initiation cascades are to be accelerated after traumatic injuries. EPO, as catalyst and systemic and topical promoter of tissue regeneration, supports, in accordance with the invention, the immunomodulatory effect initiated regionally by macrophages, which includes immunological modulation and liberation of interleukins and cytokines in macrophages in combination with plasma cells. This interaction competence according to the invention produces the high regioselectivity of the therapeutic administration of EPO/TPO at the site of need (trauma, inflammation, autoimmune disease).

In accordance with the invention, EPO coordinates this regional immunostimulation in therapeutic use with the systemic endogenous response. EPO thereby promotes the initiation of the inflammation reaction in the sense of a cascade acceleration as therapeutic effect. It increases the liberation of endogenous growth hormones and thus also controls their side-effect potential. Systemic administration of growth hormones can thus be avoided and the uncontrolled effect thereof with respect to potential tumourogenicity in the course of the physiological action situation is avoided.

Connective tissue structures can be restored in accordance with the invention. These include collagen fibres, reticular fibres, for example lymph nodes, elastic fibres and the formation of the basic substance (proteoglycans, glycosaminoglycans, hyaluronic acid, chondroitin sulfates, dermatan sulfate, keratan sulfate, heparan sulfate, heparin). The modulated connective tissue cells are the fibroblasts, reticular cells, in particular in lymphatic tissues and organs, mesenchymal cells, fatty cells, monocytes and macrophages. It is known that monocytes are able to differentiate to give macrophages. EPO is able to accelerate the macrophage defence in inflammation and in infection reaction with respect to the subsequent and necessary tissue repair and 3D regeneration.

The chemotactic functions of the macrophages are co-coordinated by EPO. The local monocytes located in the connective tissue can be included in the tissue recruitment by EPO, enabling these to make a direct contribution in the sense of systemically and locally available progenitors and for local repair.

EPO coordinates the function of the reticoenterial system (RES). This is combined in a network of reticular fibres and incorporates the endothelial cells of liver, spleen and bone marrow. In addition, EPO coordinates the lymphocyte activity, that of the plasma cells, macrophages and—in an immunomodulatory manner—that of the mast cells.

After traumatic processes, EPO couples the individual functions, known per se, of these cells to the structure synthesis and the regioselective tissue regeneration. The inflammation reactions then subside via back-coupling effects, and autoimmune phenomena, which may also be mediated via antibody formation, thus also subside. EPO is used therapeutically in accordance with the invention here as medicament.

During tissue regeneration, connective tissue structures are formed and loose connective tissue structures (subcutis of the skin, in hollow organs, non-specialized connective tissue) are built up. EPO results in the formation of the connective tissue (unordered and ordered connective tissue, the formation in bands, ligaments, fascias, tendons and the coordination with elastic structures and three-dimensional crosslinking thereof, which is mixed tissue-specifically or also becomes pronounced in a gelatinous manner).

EPO supports the synthesis of the reticular cells, which, in particular, restore the reticular connective tissue. EPO supports the synthesis of the fatty tissue and the progenitors classified therein through recruitment and use of the propagation functions of EPO.

The action according to the invention causes improvement of the supporting functions and force transfer of these connective tissue components. Improvement in substance exchange occurs, since the connective tissue carries body vessels. Improvement in the storage functions of the connective tissue structures occurs, with storage of lipids, glycosaminoglycans. EPO results therapeutically in improvement of the water and electrolyte function.

EPO causes improvement in the protective function, since mechanical barriers to pathogenic pathogens are restored. Reparative processes occur after inflammation, since the tissue structures are restored. In accordance with the invention, EPO supports parenchymal and structure regeneration.

This should be regarded in contrast to the formation of granulation tissues (as are characteristic of a so-called wound healing), which, in the sense of a wound healing, result in replacement tissues and thus only in replacement functions. This is taken to mean the formation of scar tissues and loose fibrous tissues, which can achieve defect covering, but are associated with high functional losses. In accordance with the invention, EPO here has a structure-forming process in the sense of restoration of the previous tissue. In particularly large defects, however, combinations with place marker materials can support and promote (morphologically and functionally) the structure-forming process. This has major significance for tissue engineering, since any scaffold materials used for integration (for example support materials for vessels, heart valves, transplants) can be combined with EPO. Permanent implants (non-biodegradable materials) can be coated for better tissue integration (for example metallic and ceramic prostheses).

3. Blood Vessel and Lymph Circulation System

EPO results in re-formation of the blood vessel system and also the major blood vessels—not only the capillary structures, as known to date. The structures of the major blood vessels also include the veins and arteries (greater and lesser body circulation).

EPO furthermore facilitates regeneration processes within tissue structures, which also relate to the lymph circulation system, and the lymph vessels themselves. The restoration by EPO integration relates not only to the tunica intima, the endothelium, but instead especially also the tunica media, which consists of connective tissue and muscle cells. Furthermore the tunica externa, which forms a longitudinal connective tissue layer. The various types of artery are important in the formation of the vessels. Thus, there are arteries of the elastic muscular construction type and different connective tissue structure, which are co-induced by regenerative processes, namely the membrana elastica interna and the membrana elastica externa, and the formation of vasovasal vessels. Fatty cells are integrated into the wall layers here. In the case of the arteries of the elastic construction type, EPO facilitates regeneration of the membrana elastica interna in addition to the tunica externa with the vasovasoles. In the case of the arteries of the muscular construction type, cross section 0.1 to 7 mm, EPO facilitates vigorous formation of the smooth muscles in the media. EPO furthermore facilitates the formation of the subendothelial connective tissue layer. Typical synthesis forms, such as the tunica intima, as known to date as endothelial cell component, but also especially the membrana elastica interna, the elastic phase structures, muscle cells, tunica media, membrana elastica and tunica externa, are restored. Spatially geometrical arrangements, such as the formation of muscular venoles in the region of accompanying venoles in a specific geometrical arrangement of the vicinity, are also facilitated by the therapeutic administration of EPO.

These are not 2-dimensional connection processes with a conglomerate formation push, but instead specific 3-dimensional structure formation processes. EPO and TPO are thus in accordance with the invention not equivalent to known proliferation factors in the sense of classical growth factors, but instead act rather in the sense of "3D regeneration factors".

Similar results are found in the area of EPO stimulation in veins with the formation of the tunica intima, tunica media and tunica adventitia. The vein valve structures can furthermore be regenerated in geometrical shapes, in particular in connection with scaffold materials, or also scaffolds if this is possible in extended vascular regions after traumatic injuries and degenerative processes.

In the case of relatively large volume defects, support materials can under certain circumstances also be implanted, so that the EPO action is focused on the remodelling process and integration into the organism as a whole. In the case of complete regenerative processes, however, these vessels are formed at the same time, especially in the case of parenchymal structures.

There is no restriction to various vascular structures, for example arteriovenous anastomoses. In particular, age-induced changes in the blood vessels and degenerative structures can also be revised in combination with therapeutic administration of EPO. In the ageing process, smooth longitudinal muscle structures are formed. Degenerative processes mean neostructure formation activities started in accordance with the construction principle of the tissue structures. These can be built up in tissue structures as vessels produced de novo and are not primarily pathologically changed.

The inflammation reactions can be modelled in accordance with the invention by means of administration of EPO. By means of administration of EPO, there are regeneration processes in the region of the endocardium and also the myocardium. The epicardium is a leaf of the pericardium which is set into regeneration by administration of EPO. The parietal leaf pericardium is a serous membrane which consists of a mesothelial cell layer resting on a layer of connective tissue. In the area of the heart, regeneration of the heart valves and also of the chordae tendinae occurs, in particular, if structure aids (scaffolds) are brought in combination with stem cell colonization and administration of EPO. The re-formation of the stimulus conduction system can take place after regional destruction. These also include Purkinje fibres, and the atrioventicular nodes, which can also be repaired. In addition, lymph vessels, nerves, cardiac plexuses, coronary artery structures are combined with one another.

The lymph vessels and lymph capillaries are constructed by administration of EPO corresponding to the normal shaping and collecting vessels (tunica intima, tunica medica and tunica adventitia). Regenerative processes may also relate to the region of the ductus thoraticus.

Valve and collecting vessels are folds which are likewise integrated in structural synthesis processes. In the case of the blood vascular system, activation of angioplasts occurs, some of which are recruited from peripheral progenitors, but also from regional progenitors. Initially, the conception of capillaries consisting of endothelial cell structures occurs. However, it is important in the area of application of EPO that the structure synthesis can be initiated by building up the subsequent muscular structures and connective tissue structures.

The stimulus conducting system plays a major role for the coordination of the EPO action, since it provides interactions with the modulating cells and nodes.

The cells of the immune system include lymphocytes, macrophages, plasma cells, stem cells. The mesh work of reticular connective tissue connects the cells of the immune apparatus in the immune system. Administration of EPO effects accelerated repair of the reticular connective tissue, the reticular cells and the reticular fibres. Thymus structures can likewise be repaired again. Cortical and medullary structures are restored histologically there. Administration of EPO also results in histological regeneration of lymph nodes, which in turn are able to form intermediate sinus, medullary sinus, marginal sinus, capsular and connective tissue septa, but also deferent lymph vessels, lymph nodes or medullary cords.

The histological organization after completed repair process and coordinated combination corresponds to a usual structure with capsular and connective tissue septa, hilar connective tissue and afferent/deferent lymph vessels, lymph nodes, medullary cords and deferent lymph vessels.

Regenerative principles can also result in restoration of the normal capsule, the particle structures and the hilus in the area of the spleen. Furthermore, malpighian bodies of the splenic sinus plates are found in the lactiferous cords for restoration of the white pulp. The blood circulation of the spleen is restored, with arteries of the spleen, splenic sinus veins and pulpal veins being brought together. The white pulp and the connection of the lymphoid sheaths is restored.

Administration of EPO after injuries causes a three-dimensional interaction of the basal membranes, the reticular cells, the reticular fibres and the erythrocytes. Open and closed circulation systems are formed. The interaction with macrophages, which can arise from the bone marrow cells, is of importance here for enabling initiation of endogenous cascades within the body and the mediation of growth mediators (growth hormone).

4. Skin/Cutis

Reparative processes after burns, trauma, scalds, mechanical injuries or inflammation in the area of the skin are very varied. Administration of EPO or TPO enables regeneration to be achieved with and without structural replacement structures.

In particular in the case of chronic diseases, impaired perfusion, diabetic ulcers and also phenomena of an immunological nature, EPO can engage with a modelling action here. In histological terms, re-formation of a normal epidermis, dermis and a subcutis occurs, which achieves corresponding vascularization with macrostructures. On the palms of the hands and soles of the feet, the formation of the stratum basale, stratum granulosum, stratum lucidum, stratum corneum occurs. On the dermis and outside, the formation of dermal papilla occurs. On the epidermis (inner surface), the corresponding epidermal recesses are formed again. In addition, appendages and the formation thereof from progenitors is also supported. One problem in tissue engineering to date was the connection of structural repair to the formation of skin appendages in the area of the skin.

Administration of EPO enables interaction processes to be achieved in the area of the human melanocyte system. Physiological back-coupling processes between eyes, meninx and the formation of pigmentation are taken into account, since these are not isolated cell connections, but instead organtypical regeneration products.

Reparative processes of the dermal portion include muscular structures (musculus arrector pili), tactile structures, outer root sheath of the hairs and inner root sheath and also the hair bulb structure. Under certain circumstances, this projects into the fatty tissue. In the hairs and hair follicles, connective tissue root sheaths are formed, which contains an important functional structure in regeneration. The glassy membrane, outer root sheath, inner root sheath and the final hair form therefrom. Similar processes can be supported and effected in the area of nail regeneration. Within the tissue structures, sweat glands are also formed. In the skin structures, perifollicular network structures, networks, subcapillary arterial networks, termal vein networks are formed again.

5. Digestive System

The administration of EPO effects restoration of the innermost layer of the mucous membrane, tunica mucosa and the connective tissue layer of the so-called lamina propria. The deepest layer forms a layer of smooth muscles, the lamina muscularis mucosae. The layer structure is as follows: serosa cells, then muscularis, submucosa and mucosa. These structures are passed through digestive glands, and mucous membrane glands are located in the mucosa. In addition, submucosa glands and the plexus myintericus (Auerbach) and the plexus submucosa (Meissner) regenerate. In the area of the tongue, the leaf-shaped papillae regenerate. In the area of the mouth, taste buds are also regenerated in the region of the tissue regeneration. These are built up from basal cell type 4, supporting cell type 1, receptor cell type 3, glycoproteins and taste pores. The seromucous salivary gland consists of strip pieces, connecting pieces, mucous end pieces, basal membranes, myoepithelial basket cells and serous end pieces. Important reparative processes can also take place in paradontosis in the area of the tooth region. For example, this relates to the structures of the periodontium in connection with the alveolar bone and the root canal with apex. The reparative processes can be achieved by the addition of stem cell-colonized calcium phosphate structures or other mineral replacement materials coated with EPO. The EPO-supported formations of a regeneration process takes place in the region of cysts in the area of the maxillary antrum, sunmandibular structures, after root removal and re-repair of these structures locally in vivo.

The corresponding materials and odontoblasts can likewise be prepared in vitro by administration of EPO.

Osteochondral structures, such as, for example, the osteochondral cylinder, can be prepared in vitro and implanted in vivo in a growth regeneration promoting manner with administration of EPO. The formation of the root canal structures with neoinnervation is promoted via EPO-coated guide structures which are added. Molecules of the extracellular matrix, which can also be brought about as peptide structures in coating processes, help here. The enamel organ structures together with pulpal odontoplasts, intermediate zone enamel pulp, can be supported in the growth process after injuries and traumatic processes. The reparative and regenerative processes focus on the area of the surrounding connective tissue and integration of the tooth structure or alternatively of an implant in the region of the jaw. The pulpal connective tissue and the formation with blood vessels which block in or off the apex of the root canal plays a major role for innervation here. The peridontium (root membrane) is thus regenerated. The Sharpey's fibres run through the root membrane and are anchored in the cement or alveolar bone.

EPO results in regenerative processes in this area after inflammation and traumatic reactions. In the area of the gums, administration of EPO in inflammation phenomenon in paradontosis causes improvement of the reparative process.

Throat:

Regenerative processes can also be extended to the pharyngeal area in the restoration of the plasmatic multilayered epithelium by administration of EPO. Here too, tunica muscularis and tunica adventitia can be restored in a coordinated manner. Crypt structures and capsule structures in the lymphocyte structures within the tonsils are restored. Regenerative processes can also promote regioselective regeneration of inflamed structures, as in tonsillitis.

Trunk/Intestine:

In the intestinal area, there are highly regenerative epithelial components which are able to renew themselves within 24 to 48 hours. In the case of inflammation reactions, a defect occurs in this reparative activity, so that supporting effects by EPO/TPO can facilitate a compensation reaction of the body here. This causes the re-formation of epithelial structures, such as lamina propria, tunica mucosa; lamina muscularis mucosae, tunica sub-mucosa, ring muscles, tunica muscularis and longitudinal muscles and tunica adventitia, which would run through the entire intestinal wall area as reparative processes, so that selective, superficial, also intramural and deep-mural regeneration is facilitated. These principles can be continued over the entire region of the gastrointestinal tract, starting from the throat, mouth as far as the oesophagus and into the rectum. In the oesophagus, the lamina muscularis mucosae, lamina propria and the multilayered squamous epithelium can be regenerated. Serous structures are integrated and repaired by administration of EPO.

The reconstruction of the stomach wall, in particular the area of the areae gastricae with gastric foveolae, gastric glands, lamina muscularis mucosae, on the outsides mesothelium, then sub-serous connective tissue, tunica muscularis, tunica submucosa and tunica mucosae is possible. In the structures, parietal cells, gastric glands, principal cells, lamina propria, muscularis mucosae and tunica mucosae are regenerated, likewise the surface epithelium. Regenerative processes, including in the area of the cells of the corpus fundus gland region, include the re-formation of principal cells. The connection to parietal cells is provided. The stimulation achieved in accordance with the invention by EPO also includes the regeneration of cells which liberate vasoactive substances, such as polypeptides, and the formation of enterochromaffin cells (ECN), which liberate serotonin. Gastric glands can be regenerated. It is known that the surface epithelium of the stomach can renew itself within three days. In the case of severe traumatic, inflammatory injuries, regeneration defects, the administration of EPO helps to restore this regeneration ability. In the area of the small intestine, reformation of the lamina propria, the lamina muscularis mucosa, the solitary follicles, the tunica submucosa, the ring muscles, the longitudinal muscles, the tunica serosa occurs. The intestinal villi in the structures are re-formed, as are the solitary follicle and the Kerkring's folds. The crypts are likewise restored. The crypts contain so-called Paneth's cells. These are able to form secretion generate in the gland floor. Peyer's patches is located in the lamina propria of the duodenum. The end pieces of the Brunner's glands after EPO regeneration exhibit characteristic mucous cells, a pale cytoplasm and flat cell nuclei lying on the cell bottom. Large intestine regeneration on administration of EPO plays an important role, in particular, after surgical removals.

6. Skeleton

EPO results in regeneration of the skeletal tissue with the sub-division into taut collagenic connective tissue, cartilaginous tissue and bone tissue. In the case of the chondrocytes, EPO promotes the formation of the intercellular substances and leads to functional improvements, the chondrocyte structures. EPO supports the formation of the growth zones and the formation of the pericondium (surrounding connective tissue structure, with the exception of joints) after traumatic effects. In adults, cartilage cells, as is known, can no longer multiply since the cartilage formation activity of the pericondium is restricted to the time of body growth before adult age. Administration of EPO enables these regeneration processes to be therapeutically influenced and the formation of connective tissue cells as defect filling material that otherwise occurs to be prevented. In some cases, the plastic process, i.e. the transformation of fibroblasts and chrondrocytes in the recruitment of the administration of EPO, can play a role here. Therapeutically, EPO is employed in the regeneration of cartilage structures, such as, for example, hyalinie cartilages in the area of the joint surfaces for the larynx ends, trachea, bronchi and a part of the nasal skeleton. In accordance with the invention, EPO promotes the formation of the cartilage capsules and the formation of the proteoglycans/collagens. Combination with stem cells is possible in accordance with the invention. However, EPO is also employed in isolated form in order to regenerate elastic cartilage which is localized, for example, in the epiglottic cartilage area. These also include the cartilages of the outer ear and the eustachian tube. EPO is employed in accordance with the invention in order also to restore fibrous cartilage in the connection area of joints. These include the regeneration processes in the area of the intervertebral discs, intraarticular projections, discs and meniscuses. In the adult organism, the regenerative changes in the cartilage which are otherwise lost can be re-activated in accordance with the invention, the regeneration, the reconstruction and the proteoglycan/collagen synthesis of the chondrocytes can begin again. Calcification of the cartilage can be prevented at the undesired points.

In accordance with the invention, EPO results in coordinated 3D regeneration of bone tissue as complete structure including the vessels in therapeutic areas. In the case of relatively large defects, replacement structures of inorganic or biological support materials can be introduced. Phase-pure tricalcium phosphate and an EPO coating can be combined here.

Alternatively, hydroxylapatites or biological bones of allogeneic or xenogeneic origin can be employed correspondingly after corresponding treatment. In accordance with the invention, the administration of EPO acts on the periosteum and endosteum and results in recruitment and multiplication of the progenitors located there. The formation of lamellae, the formation of osteocytes and the corresponding lacunas and canaliculi then occurs. In accordance with the invention, EPO is employed for bone regeneration, and the formation of the haversian canals, bone channels of the interstitial lamellae, the lacunas, concentric lamellae, which facilitate adjacent lamella system delimitation and connection. Surprisingly, Volkmann's canals are found as osseous pathways for the blood vessels. EPO stimulates osteoprogenitor induction, osteoblasts, osteocytes and osteoclasts. In osteoblasts, EPO results in neosynthesis and induction of the intercellular substances of the bone. The tissue formation includes the formation of bone-specific cells. EPO promotes the formation of ossification channels and the formation of bone trabeculae and the integration of vascular connective tissue structures. Starting from injuries, for example accidents, trauma, but also inflammation reactions, EPO is able to take on the tasks of coordination in the restoration of the tissue structures, resulting in the formation of zones of cartilage breakdown, bone re-formation with zones of cartilage calcification, zones of chondrocyte hypertrophy, division zones (columns, cartilages and reserve cartilage zones (high cartilage)).

In accordance with the invention, EPO promotes vasculogenesis also in the area of the bone, in particular the formation of an arteria nutricia, the metaphysitic vessels and the epiphysitic vessels. In addition, the periosteal vessels are integrated location-specifically.

EPO promotes the formation of the nucleus pulposus and annulus pulposus as well as the hyaline cartilage in the area of the intervertebral discs. In joint structures, lateral ligaments, medial ligaments and capsule reinforcement bands in the formation are promoted. Repair processes of the synovial membrane are included here. In accordance with the invention, EPO promotes the re-formation of the smooth muscles, the tightened muscles and the myocardial tissue.

7. Smooth Muscles

Histogenesis of the smooth muscle cells is promoted by EPO in the formation and differentiation to give myoblasts from mesenchymal cells. In the skeletal muscles, EPO promotes the formation of the perimysium and the endomysium. EPO causes integration and coordination of the ingrowth of motor nerve fibres and the formation of motor end plates. EPO promotes histogenesis of the cardiac muscle. The cardiac muscles normally have no or only very low regeneration ability. EPO is employed in accordance with the invention in order to achieve tissue regeneration of the smooth muscle cell structures, the skeletal muscles and the cardiac muscle tissue and to achieve an immunomodulatory remittance effect due to back-coupling. This is of importance for therapy in inflammatory autoimmune muscular diseases.

8. Nerve Tissue

In three-dimensional tissue regeneration, connection to nerve systems and innovation processes plays a major role. In accordance with the invention, EPO is used for coordination of vasculogenesis with neurogenesis and the uniting of these structures in the innovation of parenchymal glands, tissues and organs. This results in the re-formation of synaptic contacts, the formation of neurones as laminae and vertical units and the formation of nerve fibres and fibre tracts. Connective structures in the area of the ganglion plexuses are generated. The cerebral nerves and cranial nerves are included, the spinal nerves are regenerated after separations, and both efferent motor and afferent or sensory structures are reconnected again. Nerve guide rails, which may consist of biopolymers, (biodegradable or non-biodegradable (silicone, polyurethane)), or may be of biological origin, or synthetic origin (for example collagen, elastins, fibronectins, polylactide, polyhydroxybutyrates, silk), and can be used in combination with stem cells, can be employed in a supporting manner. The stem cells can be of mesenchymal origin. However, they can also be recruited directly from the tissue structures of the neuronal structures, where this is not an avoidance of apoptosis, but instead an initiation of nerve fibril growth and multiplication into a directed three-dimensional structure.

An important effect of the action of EPO is tissue regeneration in the area of the connective tissue structures of the central nervous system, in particular the meninges and the accompanying blood vessels thereof. This action is very important for regeneration of ganglia and sensory organs. In accordance with the invention, the formation of axonal structures and the formation of axons is facilitated. The electrophysiological activity and axonal transport is restored as soon as crosslinking is achieved. Combined administration with vitamins, for example vitamin C, may support these processes. However, the action according to the invention is important in tissue regeneration in the interplay between activation by local plasma cells, macrophages, lymphocytes, under certain circumstances mast cells, which result in cellular recruitment and reparative behaviour (after therapeutic administration of EPO). In the central nervous system, EPO can also be employed in accordance with the invention for regeneration in the area of degenerated structures. These include Parkinson's disease and degeneration in the striatum area and Alzheimer's disease and amyotrophic lateral sclerosis, which also radiates into the periphery, and multiple sclerosis and in organ-induced depression. Treatment with inflammation stimuli is important here, so that the activation cascade determined by EPO can be initiated. Stereotactic implantation with mesenchymal progenitors and neuronal precursor cells and also the use of local progenitors of regional and peripheral monocytes can be augmented therapeutically by EPO and driven to regeneration. The aim is the formation of new neuronal cells of the central nervous system. In accordance with the invention, the cells then start functioning, with formation of neuroactive peptides and endorphins and, for example, serotonin, dopamine, noradrenalin, acetylcholine. Synaptic processes are re-connected. In secondary functions of regeneration, the neuronal cells of the CNS, such as, for example, the protoplasmatic astrocytes, the fibrillary astrocyte, oligodendrocytes, microglia (glioblasts) and the ependyma are not included either. The nerve tissue is formed by EPO not only in neuronal regeneration, but also in the accompanying supporting cell structure of the so-called neuroglia. The neuroglial cells exceed the neuronal cells by a factor of up to 10 in proportionality. They form the connective tissue structural framework of the CNS and carry the blood vessels. This has an important regenerative component for structural reconstruction. The ependyma is taken to mean the epithelial lining of the inner surfaces of the ventricles in the CNS.

In accordance with the invention, EPO results in regeneration of the axonal sheaths, a so-called Schwann's sheath. EPO promotes the formation of the myelin sheath (medullary sheath). In the CNS, oligodendrocytes supply the myelin sheaths. This is particularly important therapeutically in diseases of medullary sheath formation. In the peripheral nerves, the accompanying cells are induced to cover ganglia. The Schwann's cells are stimulated by EPO in the area of the regeneration process also to facilitate the new formation of the peripheral nerves. The formation of the interperiodic lines of the myelin segments occurs here.

In accordance with the invention, EPO promotes the formation of the grey and white matter and tissue-specific differentiation thereof in the CNS. EPO supports the formation of ganglia (grouping of nerve cells outside the CNS). After traumatic situations, regeneration of these structures occurs. The regeneration processes, including in the regenerative area, are driven to neoinnervation via EPO modulation, where neoinnervation occurs as reparative process starting from the lachrymal gland, submandibular gland, sublingual gland and parotid gland, heart, larynx, trachea, bronchi, lung, stomach, small intestine, blood vessels of the abdominal cavity and other blood vessels, liver, gall bladder, bile ducts, pancreas, adrenal medulla, large intestine, straight intestine, kidney, bladder and genitalia. Reparative processes occur in the area of the sympathetic trunk and sympathetic trunk ganglion (ramus communicans albus and ramuns communicans griseus and nervus splancnicus, ganglium coeliacum and ganglium mesintericum superius). The nerve endings can also be integrated into the multilayered squamous epithelium structures by the regeneration processes.

Histologically, end bulb structures, corpuscles and so-called Pacini's corpuscles on the sensitive structures are restored. EPO supports the formation of the dura mater, whose structure in turn contains connective tissue guide structures of sensitive nerve blood vessels. This causes the formation of the subdural cavity (formation of the duramatis spinalis) and the epidural cavity. The dura mater encephalica adheres to the cranial bone and is reconstructed by EPO stimulation during the regeneration process. The arachnoidea extends into the subarachnoideal cavity. EPO regeneration processes also stimulate the restoration of the subarachnoideal cavity and the leptomeninx. This can form relationships to the cardiovascular (Virchow's cavity). EPO results in restoration of the thin layer of connective tissue which covers the surface of the brain and spinal medulla. Regeneration of the venous sinus of the arachnoidal villi occurs. In particular, the plexus chorioidius and the ventricle of the brain are regenerated. In inflammation processes, the EPO administration according to the invention results in re-formation of the blood-brain barrier by structural tissue regeneration. The functional significance of this regeneration, which extends over the entire cerebral tissue, including the medulla oblongata with the exception of the neurohypophysis, is of major importance for homeostasis of the CNS. The barrier is re-formed again with astrocytes by administration of EPO.

Histogenesis of the Nerve System Due to the Action of EPO

After trauma in the central nerve region and degenerative processes, the interplay between glial cells, oligodendrocytes, neurones, subdural cavity and blood vessels are disturbed. These spatial connections and the accompanying cells located therein are physiologically involved in histogenesis. Nevertheless, healing problems occur in the case of injury since the neuronal adult tissue are not capable of regeneration to the desired extent. The administration of EPO enables this process to be driven into a regenerative direction to an accelerated extent in accordance with the invention and structural restoration to be achieved by connection of the structural components to the parenchymal components. In embryonic development, this development step proceeds in accordance with a defined schedule. EPO is a mediating structure in the CNS in combination with, for example, nerve growth factor (NGF). The poor regeneration ability of the CNS in the adult organism is compensated by administration of EPO in that recruitment of the local cells, immunomodulatory cells, scavenger cells (macrophages) and stem cells can take place. Stem cells (for example autologously from peripheral blood CD45 positive cells, mesenchymal stem cells, from fatty tissue, from umbilical tissue) and other stem cells can be combined. The use of autologous tissue is preferred to the use of allogeneic cells (for example embryonic cells), should be distinguished from the EPO effect for immunological reasons, but should not be excluded).

In combination with stereotactic operations or infusions, the progenitors can be positioned location-specifically. Cut or damaged peripheral nerve fibres can be steered into the desired area by administration of EPO in combination with guide structures, guide rails or also in combination with biological structures locally (from the immediate environment), for example also by fibrin structures. Fibroblast structures can also be integrated into other areas with stem cells and EPO. Alternatively, biological matrix molecules based on collagens or elastins in recombinant form or consisting of peptide sequences, can also be introduced into mixtures, giving injection solutions, which can be mediated by administration of EPO. In parallel, the regeneration can also be supported systemically by administration of EPO. Without the administration of EPO and stem cell support, so-called Waller's degeneration, which has been known since 1850, occurs. Regeneration processes occur along the so-called Büngner's band. Terminal degeneration phenomena occur in the CNS 12 to 24 hours after a lesion. The cell body disintegrates due to chromatolysis. The regenerative processes, which are accelerated by EPO, result in axon synthesis. EPO renews the nettle matter and the Golgi apparatus. The swellings of the cell body reduce, while regeneration phenomena occur in peripheral axons in a physiological manner in the first week after a lesion. The EPO administration according to the invention causes acceleration of the regeneration, so that regeneration phenomena, such as the formation of philopodia and protoplasmatic growth clubs, are facilitated within one week. The axonal philopodia normally require two weeks in order to grow cavities into the distal segment in the Schwann's cells. In the case of complete severance, these structures can be bridged by biological structures and collagens. A use form for nerve splinting is, for example, EPO-coated collagen tubes. Other support materials, such as polylactide or polyhydroxyalkanoates, can likewise be used. Combination with stem cells and autologous or allogeneic fibrin as guide structure is possible.

In polymyolitis states, administration of EPO achieves neosynthesis of the perineurium. This promotes the formation of collateral sprouting in the CNS.

9. Liver

After viral infections of the liver (for example hepatitis A, B, C, D), regeneration defects of the liver may occur. Liver cirrhosis represents the end stage of a regeneration defect of the liver, in which binding tissue replacement of the parenchymal cells has occurred since the endogenous regeneration cannot keep pace correspondingly with the rate of noxa-induced damage due to continuous regeneration.

After trauma and surgical interventions, for example in tumour resections of the liver, acute loss of viable tissue and tissue destruction occur.

In accordance with the invention, accelerated regeneration of the hepatocytes and non-parenchymal cells of the liver as far as restitutio ad integrum occurs after administration of EPO. Characteristic of this is re-formation of a normal liver lobule architecture, re-formation of the interlobular connective tissue, the central veins and the hepatic triad: the bile ducts, lymph vessels, periportal connective tissue, arteries and vena interlobularis are evidently restored there in addition to the liver cells.

The specific formation of the intralobular reticular fibre network and the liver sinusoids is restored. The histological construction after regeneration shows the typical barred structure. The windowing in the area of the endothelial cells has a typical liver shaping. Important initiator cells after trauma are the Kupffer cells, which release IL-6, IL-1, TNF-alpha.

The administration of EPO results in significantly higher regeneration processes, even in comparison to liver tissue of ontogenetically young livers. In-vitro factor increase by a factor of 10 to 30 are achieved.

10. Gall Bladder:

In the case of inflammation of the gall bladder and also after mechanically induced injuries to the gall bladder, restoration of the normal wall structure occurs as follows on therapeutic administration of EPO: connective tissue (capsule, adhered to liver capsules), tunica muscularis, Luschka's crypts, lamina propria (richly vascularized) and tunica mucosa (with epithelium, single-layered, columnar). Lymph vessels, nerves from the area of the vagus are re-connected.

11. Pancreas Regeneration:

The administration of EPO supports regeneration of the B cells, D cells and A cells of the pancreas. The regeneration commences from the small epithelial cords emanating from the secretory ducts. The veins and arteries of the pancreas are regenerated at the same time.

The regenerative processes relate to the endocrine and exocrine component after trauma, inflammatory diseases or immunological autoimmune processes.

12. Nasal Cavity and Paranasal Sinuses:

Septum nasi, vestibulum nasi, nasal cavity, nasal mussels are subject to regenerative processes after injuries and administration of EPO. The epithelium is restored and likewise the lamina propria (taut, collagenic connective tissue with tubuloalveolar mucoserous glands), vessels with arteriovenous anastomoses and cavernous bodies, adrenergic and cholinergic nerves. In the area of the olfactory mucous membrane, the very high epithelium and the serous Bowman's glands are reconstructed.

13. Laryngeal Area:

The multilayered, columnar ciliated epithelium, the lamina propria, the serous glands and the mixed seromucous glands are restored by administration of EPO/TPO with and without combination with stem cells.

14. Trachea:

Restoration of the typical wall structure with perichondrium, hyaline cartilage, perichondrium, lamina propria and seromucous glands, submucosa, lamina propria and epithelium. The adventitia is regenerated at the periphery and the tracheal cartilages are connected by smooth muscles. The epithelium contains beaker cells, basal cells and ciliated cells. Likewise endocrine (Pa) cells, type I and type II brush cells.

15. Lungs:

The complex 3D architecture and structure of the lung is restored in accordance with the invention as follows. Ateria bronchialis, glands, bronchus, branches of the arteria pulmonalis, bronchioles, smooth muscles and branches of the vena pulmonalis, ducti alveolari, alveolar saccules and the pleura covering is brought together three-dimensionally. In the broncho-pulmonary segments, intersegmental septa, segment veins and segment arteries are regenerated. In the bronchi, epithelium, lamina propria, tunica muscularis, glands and cartilages are regenerated. In the alveoli, the blood-air barrier function is restored. Elastin structures are regenerated. Alveolar epithelial cells (type I and II) occur again. Blood vessels, lymph vessels and nerves (plexus pulmonalis) are inserted in a three-dimensionally coordinated manner by EPO and/or integration with stem cells.

16. Urinary System:

The regenerative effects in the area of the kidney have remained unknown to date, since EPO has been employed substitutively for the EPO deficiency in the case of chronically insufficient kidneys. In the case of traumatic injuries, inflammation and toxic or immunological damage, administration of EPO with and without stem cells/progenitors results in accordance with the invention in regeneration of the urological systems. In the kidney, regeneration of the cortical structure, renal calyices, the medulla, the medullary rays, renal pyramids and columna renalis occurs.

Regeneration of the mesangial matrix, the mesangium cells, the glomerulus (with lamina rara interna, lamina densa, lamina rara externa occurs. The structural relationships of the collagen filament bundles, the mesangial cells, podocytes and endothelial cells are restored. In the renal cortex, collecting tube, main part, middle part, macula densa, juxtaglomular cells and vas afferens are regenerated. In the renal medulla, re-formation of the characteristic interstitial cells and the ductus papillaris occurs.

The ureter structure is regenerated in the tunica adventitia, ring muscles and longitudinal muscles of the tunica muscularis, lamina propria, and epithelium (tunica mucosa). The bladder is driven to restoration of the epithelium, lamina propria (tunica mucosa), tunica submucosa (longitudinal and ring muscles) and outer longitudinal muscles.

The female urethra is driven to regeneration of the tunica muscularis, the venous network, the glandular lacunas, the lamina propria and the predominantly non-cornified squamous epithelium by means of EPO and/or stem cells. In the male urethra, the pars prostatica, the musculus sphincter urethrae and the diaphragma urogenitale, utriculus prostaticus, pars membranacea, pars spongiosa and the fossa navicularis is regenerated. The mucous membrane of the pars spongiosa is followed by the corpus spongiosum. After traumatic injuries or surgical interventions, EPO in combination with fibrin adhesive with and without stem cells can be injected in a connecting manner into the structural defects or correspondingly applied topically.

17. Endocrine Glands:

In the area of the pituitary gland, epiphysis, thyroid gland, parathyroid gland, pancreas (islets of Langerhans), adrenal glands, ovaries and testes, tissue injuries can occur due to traumatic injuries, operations (for example tumour resections). In these cases, EPO can in accordance with the invention lead to or support tissue regeneration in combination with stem cells from the autologous bone marrow, umbilical cord stem cells, progenitors from the peripheral blood (monocytes) or by recruitment of local progenitors. In the adenohypophysis, the basophilic cells, the arteriae hypophysales superiores and inferiores, the gomitoli and the portal vessels are restored. The neurohypophysis is regenerated in its composition with pituicytes, unmedullated nerve fibres from neurosecretory neurones in the hypothalamus. To this end, EPO-fibrin cords are in accordance with the invention laid between the regions as guide structures with stem cells. Capsule structures are regenerated as in other cerebral regions. In the epiphysis, the habenula, recessus pinealis, lobular structures, brain sand, connective tissue septa and pia mater (capsule) is restored. Nerve fibres, pinealocytes, astreocytes are bound into the specific structures of the epiphysis.

The thyroid gland is subject to frequent surgical interventions. The follicular epithelial cells, C cells, connective tissue structures are regenerated correspondingly.

After the regeneration according to the invention, adrenal glands consist of capsule, zona glomerulosa, zona fasciculata, zona reticularis. Spongiocytes are located in the zona fasciculata.

18. Reproductive System:

Regenerative repair processes can in accordance with the invention lead to restoration of the functional structure through structural processes in ovaries. To this end, in particular, the regeneration processes of the stroma ovarii, the tunica albuginea, the granulosa cells, theca folliculi interna and externa are involved. The mesothelial lining is closed again after injuries. In the fallopian tubes, the wall structure is restored (epithelium, lamina propria (mucous membrane)), ring muscles, longitudinal muscles (muscular layer), subserous connective tissue, mesothelium (serosa)).

In the ampulla of the fallopian tube, gland cells, lamina propria and ciliated cells are regenerated. The corpus uteri is regenerated structurally in the endometrium, myometrium and perimetrium. The mucous membrane (epithelium, lamina propria), muscular layer (longitudinal muscles, musculus bulbospongiosus) and adventitia of the vagina are regenerated. Lymph vessels and nerve supply are restored. In addition to the entire tissue area of the female genitalia, as in the male genitalia, repair processes after trauma and other injuries are possible. Thus, inter alia, testes, epididymis, penis (including corpus cavernosum), ductus seminiferus, prostate and the structural incorporation thereof into the surrounding soft and hard tissue can be regenerated in a coordinated manner. The blood-supplying structures, lymph vessels and nerves are re-integrated.

19. Mammary Gland:

The structured synthesis into lobules, connective tissue, lactiferous sinuses, secretory ducts with the histological detailed structure alveoli, intra- and interlobular connective tissue, milk duct, myoepithelial cells takes place again by regeneration. In particular after tumour resections or plastic interventions, the mammary gland tissue can be reconstructed in combination with biologically modellable scaffolds, EP and stem cells.

20. Central Nervous System:

In the brain and spinal cord area, mechanical and ischaemic insults with subsequent tissue degeneration or structure interruptions, in particular, play a clinically important role. Grey and white matter, cerebellum, mesencephalon and cerebrum, nuclear zones and fibre tracts are united structurally and regenerated.

The diencephalon includes the epithalamus, thalamus dorsalis, subthalamus and hypothalamus. The region of the telencephalon encompasses cytoarchitectonically about 50 fields which have to be structurally regenerated. The main regions are the frontal lobes, temporal lobes, parietal lobes and occipatal lobes. The septum regions, the bulbus olfactorius and the cortical regions can be regenerated. The regeneration area of the basal ganglia includes the corpus striatum with nucleus caudatus and putamen, the ventral striatum, and nucleus accumbens and the nucleus basalis. The regeneration processes enable the failures of motor areas with the associated paralysis and the failures of sensory neurones to be revised. Damage in the region of the motor cortex (for example due to birth traumas and accidents) with resultant spastic paralysis can be revised. In the case of damage to the anterior horns with associated flaccid paralysis, regenerative processes can likewise be induced. Defects in the hippocampus functions cause severe defects in the area of spatial awareness and memory (Korsakoff's syndrome). In the case of damage to cortical neurones, the associated risk of the development of Alzheimer's can be reduced. In the case of cerebrovascular insufficiency or even cerebral infarction, reparative processes can be initiated by regeneration.

21. Eye:

The regeneration processes extend to the cornea, conjunctiva, iris, Schlemm's canal, ciliary muscle, lens, zonular fibres, ora serrata, musculus rectus medialis, vitreous body, retina, vessels, dura mater, arachnoidea, optic nerve, arteria and vena centralis retinae, retina, choroidea and sclera. The specific structure of the cornea with collagen lamellae, fibroblasts, elastin fibres, collagen lamellae, Bowmann's membrane, epithelial layer is restored. The sclera is regenerated into lamina fusca, substantia propria and episclera. Lens epithelia, eyelids with epidermal and dermal components, subcutis, sweat glands, hair follicles, epithelium, lamina propria, tarsus, Melborn's gland, Moll's gland, musculus levator palpebrae, musculus orbicularis oculi is restored.

22. Ear:

Ear muscles, middle ear, eardrum, tympanic cavity, auditory ossicles, musculus stapedius, musculus tensor tympani, antrum mastoideum, cellulae mastoideae and eustachian tube, inner ear and osseous labyrinth, cochlea with the associated nerves, labyrinth and correspondingly Corti's organ are included in accordance with the invention in the regenerative processes.

II. Working Examples

1. Cell Transplantation

Hepatocytes:

Liver cells are isolated from non-transplantable organs or resected liver in the usual manner by collagenase digestion. (Bader, A., Rinkes, I. H. B., Closs, I. E., Ryan, C. M., Toner, M., Cunningham, J. M., Tompkins, G. R., Yarmush, M. L. (1992) A stable long-term hepatocyte culture system for studies of physiologic processes: Cytokine stimulation of the acute phase response in rat and human hepatocytes. Biotechnol Prog. 8, 219-225.)

The isolated or precultivated cells are stored in liquid nitrogen. After thawing of the cells in accordance with known protocols (Karim, N., Allmeling, C., Hengstler, J. -G., Haverich, A., Bader, A. (2000) Diazepam metabolism and albumin secretion of porcine hepatocytes in collagen-sandwich after cryopreservation. Biotechnol Letters 22: 1647-1652), suspension/cultures comprising 100-150 IU/kg/BW of epoietin alfa (based on the recipient) are added to the hepatocytes. To this end, epoietin alfa is added in a sterile solution in a volume of 1-1.5 ml of a 10 ml hepatocyte suspension having a concentration of 2-10 million cells/ml.

This suspension is slowly (1 ml/minute) injected intraportally. 1000 IU of heparin may additionally be added to the suspension in order to prevent clotting.

Alternatively, the cell/EPO mixture may also be injected under the liver capsule or directly into the liver parenchyma at a plurality of points. For this purpose it is advisable to increase the concentration of the hepatocytes by a factor of 2-5 and to reduce the injected volume correspondingly.

The puncture channels are sealed with commercially available fibrin adhesive (Baxter Tissucol). Alternatively, a tamponade with collagen fleece can be used. The epoietin alfa solution can likewise be added to the tamponade. It must be ensured that the tamponade still remains dry at the adhesion site.

The fibrin adhesive represents a 2-component mixture. One component usually consists of fibrinogen and the other of an activation solution comprising $Ca^{++}$ and proteinase inhibitors (for example aprotinin). Epoietin alfa can be added to the activation solution by mixing-in to a final concentration of 100-150 IU/kg/BW.

Stem cells from the bone marrow, the fatty tissue, a specific parenchyma or the blood (purification from Buffy Coats, CD 34 positive cells) from umbilical cord blood and the mesenchymal cells from the umbilical cord tissue can be used analogously.

In parallel to cell transplantation into ischaemically, toxically, infectiously or mechanically (traumatically) damaged areas, the cells can be introduced into a fibrin adhesive or autologous plasma and brought to polymerization with addition of epoietin alfa (100-150 IU/kg/BW).

In parallel, administration of EPO of in each case 10,000 IU s.c. can be begun, so that in total 40,000 IU are administered within one week.

The result is tissue regeneration increased by a factor of 2-3, resulting in a structural repair.

2. Postoperative Administration

After extended operations in the cardiothoracic vascular area, visceral surgery, plastic surgery, but also defect situations arising after extended trauma which may result in a vital risk to the patient.

Epoietin alfa is administered here in a concentration of 100-150 IU/kg/BW.

The administration of EPO results in an endogenous increase in growth hormone by a factor of 2, resulting in tissue regeneration after the operation being accelerated. The restitutio ad integrum occurs about 1-2 weeks earlier than in patients treated comparatively without administration of EPO.

EPO can also be administered in order to induce liver regeneration after a split liver transplant or liver transplant.

After a liver transplant, the transplanted tissue—or in the case of liver donors—the remaining tissue is not available as active tissue sufficiently rapidly and in sufficient quantity. In this case, 100-150 IU/kg/BW of epoietin alfa can be administered as much as 24 h before the operation and at the time of the operation and thereafter at 24 h intervals. This results in significantly accelerated liver regeneration, it being possible to diagnose a post-operative increase in volume in ultrasound, in particular on days 4-5.

3. Administration After Surgical Liver Resection in the Case of Benign and Malignant Tumours In an extended liver resection, there is a need to achieve accelerated regeneration since the availability of an adequate cell mass is important for the survival of the patients. After surgical resection, 100-150 IU/kg/BW of epoietin alfa can be given in the case of systemic administration or a corresponding amount in the case of topical administration (in fibrin adhesive, plasma).

If persistent tumour infestation or non-resectable tumour metastases are suspected, conventional cytostatics can be administered in combination with EPO both systemically and also topically corresponding to the tumour type and the prognosis.

After resection and administration of EPO, accelerated size growth of the treated group by 30% compared with an untreated group occurs. Especially the hepatocytes in the resection areas enter into the structural growth process to an increased extent. Complete formation of the vascular tree and the surrounding tissue occurs. The hepatocytes here are arranged in a typical manner corresponding to the normal organ in lobuli with vascular supply, cell plates with non-parenchymal cells (Kupffer, Pit, Ito and endothelial cells).

Systemic size growth occurs. The size growth ends when the initial size is reached.

The group with perioperative administration of EPO has an approximately 0.5 g/dl higher Hb value only 1-2 days postoperatively. This should be regarded as an indication of the known action of EPO. In parallel, however, liver regeneration occurs. Not only the hepatocytes, but all cell types and especially also the connective tissue structures, which represent the architecture structure of the liver, multiply here.

Experimental Procedure:

28 female pigs (weight 40.0-62.0 kg) were divided into three groups in accordance with the chance principle. The partial removal of the liver on the left side was carried out using the technique of stomach endoscopy.

The control group (n=16) was not given EPO. Group 2 (n=6) was given a combination of 10,000 units of EPO and a fibrin sealant (Quixil) locally to the liver resection surface. Group 3 was treated in the same way; however, the pigs additionally received 10,000 units of EPO systemically on days 0, 3, 7 and 11 for local EPO treatment.

Liver samples were taken from the cut-out piece of liver on day 0, 24 hours after resection from an area 1 cm below the resection surface and 14 days after resection below the resection surface and the right lobe.

For determination of Ki-67 antigen, PCNA (proliferating cell nuclear antigen) and apoptosis, the streptavidin-biotin immunoperoxidase assay was carried out on liver tissue fixed with formalin and embedded in paraffin wax.

Results

|  | Group 1 (control n = 16) | Group 2 (growth factor locally) | Group 3 (growth factor locally and systemically) |
|---|---|---|---|
| Liver volume (ml) | 892.071 ± 130.56 | 894.02 ± 104.705 | 1073.10 ± 190.13* |
| Liver weight (g) | 1001.55 ± 155.76 | 1027.18 ± 166.95 | 1249.42 ± 222.51* |
| Hb (mmol/l) (day 14) | 6.0077 ± 0.65 | 6.550 ± 0.89 | 6.58 ± 0.5541 |
| Pig weight (kg) | 48.37 ± 5.25 | 52.67 ± 6.76 | 50.54 ± 9.801 |

|  | Group 1 control group | Group 2 growth factor locally | Group 3 growth factor locally and systemically |
|---|---|---|---|
| Ki 67, day 14 (%) | 1.85 ± 2.01 | 14.0 ± 12.11* | 15.08 ± 15.71* |
| PCNA (%) | 25.33 ± 9.82 | 29.87 ± 7.18 | 37.16 ± 14.32 |
| Apoptosis (%) | 0.56 ± 0.429 | 0.267 ± 0.103 | 0.56 ± 0.30 |

Arithmetic mean and standard deviation * $p \leq 0.05$

4. Optimized Endoprosthesis or Implants

Implants can consist of biodegradable, but also permanent materials. An example thereof are metallic endoprostheses, for example in the hip area. After production of the metallic rough mould, microstructuring is achieved by abrasion, etching or laser treatment. This enables open porosities and roughnesses in the range from 0.1 to 50-60 µm to be produced.

These structures are subsequently filled in a solution of phase-pure beta tricalcium phosphate, so that a homogeneous surface coating is achieved. The structures are then ideally subjected to a continuing sintering process in order to solidify the beta-TCP structures.

Soluble salts/sugars can be incorporated into the mineral structures or gas formations induced in order to achieve further interconnecting porosities. After this manufacturing process, the structures are impregnated or coated with the growth factor according to the invention or derivatives, parts or analogues thereof. Depots can be placed correspondingly on the surfaces by filling the cavities with EPO or using slow-release substances. Alternatively, the implant removed in a sterile manner from the packaging can also be coated with EPO and analogues thereof immediately before implantation.

This results in an improved tissue connection process to the implant. The bone is connected macrovascularly and the implant is integrated osseously in an accelerated and permanent manner.

Implants in the oral, mandibular and facial area can be prepared in similar form (tooth implants).

Combination with cellular colonization in bioreactors with stem cells is possible.

Biological implants (vessels, heart valves, skin) and membranes can likewise be coated with EPO and or GH and or TPO.

5. Treatment of Osteoporosis

EPO-coated tricalcium phosphate granules are introduced into deficient/rarefied intervertebral bodies in an autologous plasma solution by means of needle puncture. The granules there are reconstructed into endogenous bone in an accelerated manner, and the degeneration process is converted into an anabolic effect.

The effect can be used in the case of intervertebral bodies which are at acute risk of collapse. Combination with a colonization process, advantageously with stem cells from the autologous bone marrow or the periosteum and blood and/or fatty tissue.

6. Indication of Cartilage Regeneration

Cartilage cells represent highly bradytrophic tissue. Regional trauma and abrasion cause inflammation processes which can lead to arthritis. Administration of EPO into the joint gap or systemically and/or in combination with cellular transplants of chondrocytes or osteochondral cylinders promotes tissue regeneration and structural reconstruction. Combined systemic or subcutaneous administration of 10,000 IU/day is possible.

7. Indication of Skin Diseases

Poorly healing wounds are coated in accordance with the invention with EPO or TPO (derivatives, analogues, parts) after preparation of the wound bed. To this end, a mechanical débridement is preferably carried out. 10,000 IU of EPO are introduced into the blood coagulum. This process can be repeated until the wound base is clean.

The structural growth begins after 2-3 days results in accelerated formation of a granulation tissue.

8. Indication of Inflammatory Intestinal Diseases

In inflammation phenomena of the intestinal tract with weight loss and anaemia, it has been found that the anaemia is not a secondary phenomenon due to poor nutrient absorption, but may be an accompanying phenomenon of an original EPO deficiency. The administration of EPO in 10,000 IU/day results in an improvement in intestine restoration/regeneration.

9. Indication of Neuroregeneration

After severance of the spinal cord, EPO results in structural growth of the neurones and re-sprouting of the axons. The administration of vitamin C has a supporting action.

EPO can be administered regionally in combination with fibrin adhesive/autologous plasma and/or endogenous stem cells (bone marrow, blood CD 34, from fatty cells, periosteum, umbilical cord).

10. Indication of Parkinson's/Example of a Chronic Disease with Inflammation Reaction That has Already Subsided Autologous macrophages stimulated by stimulation with degradable particles are integrated stereotactically into degenerated areas. In parallel, EPO (10,000 IU) is injected into the area in combination with autologous stem cells (0.3 ml). In parallel, EPO is administered systemically over the course of 2 weeks. This stimulation principle of induction of an inflammation by macrophages can also be employed in other chronic diseases in which there is no acute trauma or acute inflammation reaction.

11. Wound Healing After Burns

In 8 burned patients, the donor site of the skin graft healed 50% more quickly on administration of EPO. Two second-degree (grade 2B) burn wounds in the face healed without scarring if EPO was given to the patient. Without administration of EPO, wounds of this type healed with scarring.

The invention claimed is:

1. A method for healing of dermal wounds in an individual, the method comprising mechanically debriding the wound bed, and then introducing EPO into the blood coagulum by topical administration.

2. The method according to claim 1, characterized in that the EPO has additional glycosylation sites compared with native EPO.

3. The method according to claim 1, characterized in that the EPO is conjugated with polyethylene glycol.

* * * * *

UNITED STATES PATENT AND TRADEMARK OFFICE
CERTIFICATE OF CORRECTION

| | | |
|---|---|---|
| PATENT NO. | : 7,910,547 B2 | Page 1 of 1 |
| APPLICATION NO. | : 10/583879 | |
| DATED | : March 22, 2011 | |
| INVENTOR(S) | : Bader | |

It is certified that error appears in the above-identified patent and that said Letters Patent is hereby corrected as shown below:

Cover page, under Foreign Application Priority Data, replace "103 61 813" with
        --103 61 813.9--;

Under Foreign Application Priority Data, replace "03029961"
    with --03029961.4--.

Signed and Sealed this

Thirty-first Day of January, 2012

David J. Kappos
*Director of the United States Patent and Trademark Office*